United States Patent
Semsar

(10) Patent No.: US 11,923,088 B2
(45) Date of Patent: Mar. 5, 2024

(54) ARTIFICIAL INTELLIGENCE-BASED PERSONALIZED HEALTH MAINTENANCE SYSTEM TO GENERATE DIGITAL THERAPEUTIC ENVIRONMENT FOR MULTI-MODAL THERAPY

(71) Applicant: AR & NS INVESTMENT, LLC, Newport Coast, CA (US)

(72) Inventor: Neda Semsar, Newport Coast, CA (US)

(73) Assignee: AR & NS INVESTMENT, LLC, Newport Coast, CA (US)

( * ) Notice: Subject to any disclaimer, the term of this patent is extended or adjusted under 35 U.S.C. 154(b) by 397 days.

(21) Appl. No.: 16/556,530

(22) Filed: Aug. 30, 2019

(65) Prior Publication Data
US 2021/0065898 A1    Mar. 4, 2021

(51) Int. Cl.
| | |
|---|---|
| *G16H 50/20* | (2018.01) |
| *A61B 18/18* | (2006.01) |
| *A61B 90/50* | (2016.01) |
| *A61N 2/00* | (2006.01) |
| *G16H 10/40* | (2018.01) |

(52) U.S. Cl.
CPC ............. *G16H 50/20* (2018.01); *A61B 18/18* (2013.01); *A61B 90/50* (2016.02); *A61N 2/00* (2013.01); *G16H 10/40* (2018.01)

(58) Field of Classification Search
CPC ....... G16H 10/00–80/00; G06F 1/00–2221/00; G06Q 10/00–2250/00
See application file for complete search history.

(56) References Cited

U.S. PATENT DOCUMENTS

| | | | | |
|---|---|---|---|---|
| 2005/0216243 A1* | 9/2005 | Graham | ................. | G16H 40/67 703/11 |
| 2005/0228209 A1* | 10/2005 | Schneider | ............. | A61B 5/246 600/13 |

(Continued)

OTHER PUBLICATIONS

Duff et al., "An Adaptive Mixed Reality Training System for Stroke Rehabilitation," IEEE Transactions on Neural Systems and Rehabilitation Engineering, vol. 18, No. 5, Oct. 2010 531; Digital Object Identifier 10.1109/TNSRE.2010.2055061 (Year: 2010).*
Axilum Robotics—Robot for transcranial magnetic stimulation; https://web.archive.org/web/20190213074905/https://www.axilumrobotics.com/en/ (Year: 2019).*

(Continued)

*Primary Examiner* — Jonathon A. Szumny
(74) *Attorney, Agent, or Firm* — CHIP LAW GROUP

(57) ABSTRACT

A personalized health maintenance system, includes reading of an input-output data pair of each medical diagnosis test of a plurality of different medical diagnosis tests conducted for a first user; and cross-correlate a plurality of results of each medical diagnosis test of the plurality of different medical diagnosis tests to find a relationship among the plurality of different medical diagnosis tests for the first user. A coherent health state of the first user is determined based on the cross-correlation of the plurality of different medical diagnosis tests. The personalized health maintenance system includes a robotic system configured to output a first digital therapeutic environment around the first user. The first digital therapeutic environment is a human-sense stimulating mixed reality environment that induces a specific stimulus to the first user for remediation of at least one condition of the determined coherent health state of the first user.

14 Claims, 7 Drawing Sheets

(56) References Cited

U.S. PATENT DOCUMENTS

| | | | | |
|---|---|---|---|---|
| 2006/0161039 | A1* | 7/2006 | Juliana | A61N 2/006 600/9 |
| 2009/0299762 | A1* | 12/2009 | Martin | G06Q 10/10 705/2 |
| 2010/0130811 | A1* | 5/2010 | Leuthardt | G16H 20/10 600/27 |
| 2015/0339442 | A1* | 11/2015 | Oleynik | G16H 50/70 705/3 |
| 2017/0323485 | A1* | 11/2017 | Samec | A61B 5/14532 |
| 2019/0019581 | A1* | 1/2019 | Vaughan | G16H 50/20 |
| 2019/0043619 | A1* | 2/2019 | Vaughan | G16H 50/30 |
| 2019/0065970 | A1* | 2/2019 | Bonutti | A61B 5/021 |
| 2019/0172587 | A1* | 6/2019 | Park | G06F 17/18 |
| 2019/0189259 | A1* | 6/2019 | Clark | G16H 10/60 |
| 2019/0192874 | A1* | 6/2019 | Shukla | A61B 34/25 |
| 2019/0198169 | A1* | 6/2019 | T | G16H 50/50 |
| 2019/0207814 | A1* | 7/2019 | Jain | G06N 20/00 |
| 2019/0346925 | A1* | 11/2019 | Daniels | G06F 3/012 |
| 2020/0023157 | A1* | 1/2020 | Lewis | A61B 5/6803 |
| 2022/0247678 | A1* | 8/2022 | Atwal | H04L 63/0428 |

OTHER PUBLICATIONS

Libin et al., "Robots Who Care: Robotic Psychology and Robotherapy Approach," Published in AAAI Fall Symposium: Caring Machines—2005. (Year: 2005).*

Scoglio et al., "Use of Social Robots in Mental Health and Well-Being Research: Systematic Review," J Med Internet Res 2019;21(7):e13322) doi:10.2196/13322. (Year: 2019).*

Atar et al., "Use of the Robots, Virtual Reality and Other Technological Devices in Rehabilitation," Eur Arch Med Res 2018; 34 (Suppl. 1): S51-S54; DOI: 10.5152/eamr.2018.64936. (Year: 2018).*

Fiske et al., "Your Robot Therapist Will See You Now: Ethical Implications of Embodied Artificial Intelligence in Psychiatry, Psychology, and Psychotherapy," J Med Internet Res 2019;21(5):e13216 (Year: 2019).*

Senanayake et al., "Emerging Robotics Devices for Therapeutic Rehabilitation of the Lower Extremity," 2009 IEEE/ASME International Conference on Advanced Intelligent Mechatronics; Suntec Convention and Exhibition Center; Singapore, Jul. 14-17, 2009. (Year: 2009).*

* cited by examiner

ARTIFICIAL INTELLIGENCE-BASED PERSONALIZED HEALTH MAINTENANCE SYSTEM TO GENERATE DIGITAL THERAPEUTIC ENVIRONMENT FOR MULTI-MODAL THERAPY

FIELD OF TECHNOLOGY

Certain embodiments of the disclosure relate to personalized health maintenance systems and technologies. More specifically, certain embodiments of the disclosure relate to an artificial intelligence-based personalized health maintenance system and method to generate digital therapeutic environment for multi-modal therapy.

BACKGROUND

Advancements in medical technologies have revolutionized health sciences increasing human life expectancy, but at the same time, more and more people are becoming seriously ill. Unhealthy eating habits, erratic sleeping habits, stressful work schedule, lack of exercise, exposure to environmental pollution, harmful chemicals, UV radiation, delay in diagnosis of a condition etc. have been found to be a precursor as well as a significant contributor to many medical conditions or diseases. In today's world, the availability of sophisticated technologies and compounding scientific advancements has raised the public's expectations of what the standard of health care should be. It has become unrealistic and impractical to project these expectations solely onto the current model of practicing medicine. For example, quality of health services still largely depends on the experience and competence of a physician, and typically doctors try a trial and error method to find a right medicine and dosage for a patient in the current model of practicing medicine. Moreover, more and more research has established that some people may need another type of therapy than other people because they have certain genes or may be subjected to different environmental factors. A new understanding that diseases develop differently in different people opens up for various possibilities and ways of treating and preventing illnesses. The available solutions for personalized health maintenance still operate in bits and pieces ignoring many important facets of an individual own unique characteristics, requires a lot of human intervention (e.g. improper judgement of medicine dosages leading to unwanted or increased side effects), and lacks a wholistic and integrated approach in personalized health maintenance.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY OF THE DISCLOSURE

An artificial intelligence-based personalized health maintenance system and method to generate digital therapeutic environment for multi-modal therapy, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION OF THE DISCLOSURE

Certain embodiments of the disclosure may be found in an artificial intelligence-based personalized health maintenance system to generate digital therapeutic environment for multi-modal therapy. There are various therapies that affect physical or biological processes of the body. Examples include but are not limited to, medications, diet control, physical activity, or stress management. Multiple therapeutic modalities (or approaches), such as physiological, behavioural, social, may be used either in conjunction with medicines or without medicines for human well-being and health, and to control biological-based disorder. Typically, when human beings exercise, or do recreational or any other physical or non-physical activities that makes them feel good, the body releases certain chemicals, for example, endorphins. These endorphins interact with the receptors in human brain that reduce the perception of pain. Endorphins also trigger a positive feeling in the body, similar to that of medicines that are used to reduce/control pain and stress. Similarly, dopamine and oxytocin released provides a feeling of euphoria, affection and attachment. Dopamine is also known to stimulate the same area of the brain activated by addictive chemicals like heroin and cocaine.

The personalized health maintenance system is able to electronically create a digital therapeutic environment, which may be used specifically for an individual or for group (family or non-family) therapy. Such created digital therapeutic environment may then foster certain feeling and neuropsychological reaction in human body similar to a specific medicine (but without intake of the medicine or a reduced intake of the medicine), resulting in release of well-being chemicals. The personalized health maintenance provides technology that have the potential to become an enhanced or alternative form of treatment for diseases without the need of taking medicines or at least complement and improve the existing model by reducing the usage and dosage of medicines, and thereby avoiding or reducing the side effects of medicines. In the following description, reference is made to the accompanying drawings, which form a part hereof, and in which is shown, by way of illustration, various embodiments of the present disclosure.

Figure 1:
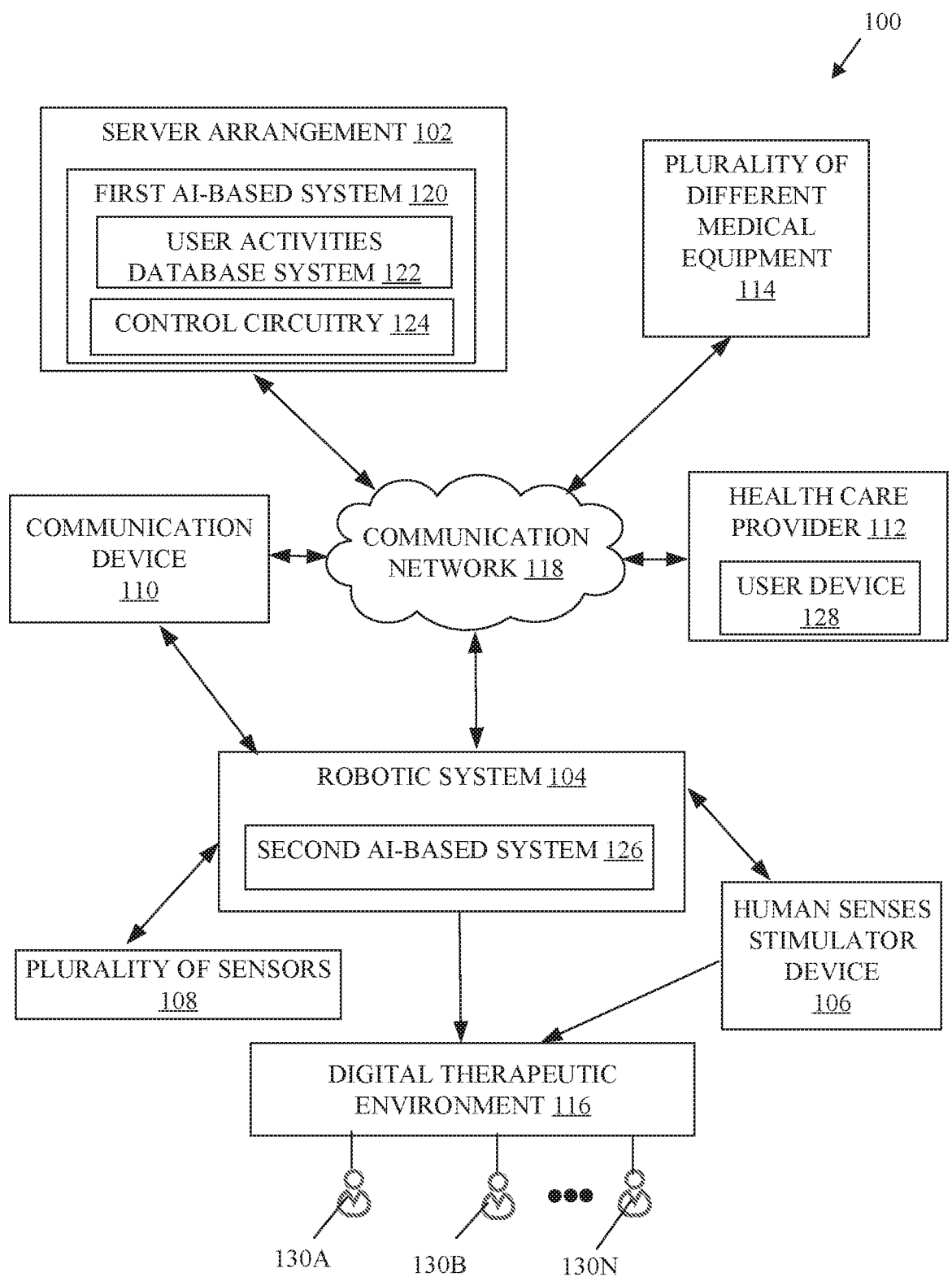
FIG. 1 is a block diagram that illustrates an exemplary environment of a personalized health maintenance system, in accordance with an embodiment of the disclosure.

FIG. 1 is a block diagram that illustrates an exemplary environment of a personalized health maintenance system, in accordance with an embodiment of the disclosure. With reference to FIG. 1, there is shown an exemplary network environment of a personalized health maintenance system 100. The personalized health maintenance system 100 includes a server arrangement 102, a robotic system 104, a human senses stimulator device 106, and a plurality of sensors 108. There is further shown a communication device 110, a health care provider 112, and a plurality of different medical equipment 114, and a digital therapeutic environment 116 generated by the robotic system 104, and a communication network 118.

The server arrangement (server system) 102 may include a first artificial intelligence (AI)-based system 120 which includes a user activities database system 122 and control circuitry 124. The robotic system 104 may include a second AI-based system 126. One or more electronic devices, such as a user device 128 may be owned, managed, and/or operated by the health care provider 112. A plurality of users 130A, 130B, . . . , 130N may be associated with the robotic system 104 and may experience the digital therapeutic environment 116. Various devices in the network environment of the personalized health maintenance system 100 may be communicatively coupled with each other, via the communication network 118.

The server arrangement 102 includes suitable circuitry, interfaces, and/or logic configured to receive health information related to a plurality of different medical diagnosis tests conducted from the plurality of different medical equipment 114. The server arrangement 102 is configured to read an input-output data pair of each medical diagnosis test of the plurality of different medical diagnosis tests conducted for each user of the plurality of users 130A, 130B, . . . , 130N. The server arrangement 102 may be configured to convert the input-output data pair of the plurality of different medical diagnosis tests into an AI system-readable data format. Examples of the server 102 may include, but are not limited to, an application server, a cloud server, a web server, a database server, a mainframe server, or a combination thereof. Further, it should be appreciated that the server arrangement 102 may be a single hardware server or a plurality of hardware servers operating in a parallel or distributed architecture.

The robotic system 104 includes the second AI-based system 126 that is communicatively coupled to the first AI-based system 120. The robotic system 104 includes suitable circuitry, interfaces, and/or logic configured to output a first digital therapeutic environment (e.g. the digital therapeutic environment 116) around a user. In some embodiments, the robotic system 104 may be configured to receive control instructions, in online mode, from the server arrangement 102 to control the output of a first digital therapeutic environment (e.g. the digital therapeutic environment 116). In some embodiments, the robotic system 104 may be configured to manage the output of the first digital therapeutic environment (e.g. the digital therapeutic environment 116) on its own, in absence of online connectively or when an offline mode is set at the robotic system 104.

The human senses stimulator device 106 may be provided as a separate device, which may be communicatively coupled to the robotic system 104, via the communication network 118. In some embodiments, the human senses stimulator device 106 may be integrated with the robotic system 104. The robotic system 104 may be configured to communicate different types of control signals to the human senses stimulator device 106. The human senses stimulator device 106 includes suitable circuitry, interfaces, and/or logic configured to generate a single sense stimulating output to stimulate a specific sense of a plurality of human sense or a multi-sense stimulating output to concurrently stimulate at least two senses of the plurality of human senses, based on a particular type of the control signal that is received from the robotic system 104.

The plurality of sensors 108 includes suitable circuitry, interfaces, and/or logic configured to capture daily activities for the plurality of users 130A, 130B, . . . , 130N. The plurality of sensors 108 may be further configured to sense a response to a specific stimulus provided by the output of the first digital therapeutic environment (e.g. the digital therapeutic environment 116) around a user. In accordance with an embodiment, the plurality of sensors 108 may include a set of external response sensors and a set of internal response sensors. The set of external sensors may refer to sensors that may be configured to sense and measure a level of an external response discernible from external surface of the body of a user as a result of the application of a stimulus by the robotic system 104. Examples of the external responses that may be sensed and measured by the set of external sensors may include, but are not limited to, change in facial expressions, change in gestures, and/or one or more sounds made by the user. In one example, the set of external sensors may comprise an imaging device, a light detection and ranging (LiDAR) sensor, and/or a radio detection and ranging (RADAR) sensor for sensing changes in facial expressions and gestures of the user when stimulus is provided to the user. The set of external sensors may further comprise an audio sensor for sensing the one or more sounds made by the user when the stimulus is provided to the user.

The set of internal sensors of the plurality of sensors 108 may be configured to sense and measure a level of an internal response generated in a body of a user due to the application of a stimulus. Examples of the internal responses that may be sensed and measured by the set of internal sensors may include, but are not limited to, nerve conduction, neuron firing, activity in muscles or nerves, activity in brain, blood pressure, heart rate, breathing rate, body temperature, and/or pulse rate. In one example, the set of internal sensors may comprise an electromyograph for sensing and measuring activity in muscles and nerves. The set of internal sensors may further comprise a blood pressure monitor, a heart rate monitor, a pulse rate monitor, a temperature sensor, an implantable chip to monitor internal organs, and/or the like.

The communication device 110 may correspond to a telecommunication hardware (e.g. a relay node or a repeater device). Examples of the communication device 110 may include, but are not limited to a 5G-capable repeater device, an Evolved-universal terrestrial radio access-New radio Dual Connectivity (EN-DC) device, a New Radio (NR)-enabled device, or a mmWave-enabled telecommunication device. The communication device 110 may facilitate communication in both sub 30 gigahertz to above 30 gigahertz. In one example, the communication device 110 may receive/transmit the RF signals from/to a base station or from another network node.

The health care provider 112 may be an individual, institution, or agency that provides health services to health care consumers. For example, a physician, nurse, dentist, mental health worker, birth control counselor, and the like, may be considered the individual that provides the health care. The institution or agency may be a hospital, a clinic, a diagnostic center, or a genetic screening laboratory or any entity that provides health care to users. The user device 128 may be associated with the health care provider 112. Examples of the user device 128 may include, but are not limited to a smartphone, a human machine interface (HMI), a handheld device, a consumer electronic device, and other computing device. In some embodiments, the user device 128 may be a part of a machine, for example, a medical equipment.

The plurality of different medical equipment 114 may refer to medical diagnostic devices from which health information may be acquired by the server arrangement 102 via the communication network 102. For example, health information may be received from a glucose meter, blood pressure monitor, imaging systems etc., each transmitting data in different formats and through different wired or wireless connections. In some embodiments, the plurality of different medical equipment 114 may communicate health information in response to a request for such health information by the server arrangement 102. Alternatively, in case of a same manufacturer, some of the plurality of medical equipment 114 may communicate health information in the same format. Examples of the plurality of different medical equipment 114, may include but are not limited to genetic testing equipment, genome or exome sequencers, blood glucose monitor, blood pressure monitor, sphygmomanometers, ophthalmoscopes, otoscopes, electrocardiograph, gastroscope, ultrasound, X-Ray unit, colonoscope, electrosurgical Unit, pulsoximeter, hematology analyzer, urinalysis system, coagulometer, laparoscopy system, magnetic resonance imaging (MRI), CT-scanner, mammograph, and angiography system. In accordance with an embodiment, any type of health information may be received from the plurality of medical equipment 114. For example, the data may include information regarding a patient, such as the patient's biological and biometric information, the patient's behaviors, results of analysis of physical patient parameters, and information regarding the patient's environment.

The digital therapeutic environment 116 may be a human-sense stimulating mixed reality environment that induces a specific stimulus to a user (e.g. the first user 130A) for remediation of at least one medical condition. The digital therapeutic environment 116 may be electronically generated mixed reality environment having therapeutic properties, as it can accelerate generation of well-being chemicals or hormones by activating certain areas of brain or de-novo facilitate generation of such well-being chemicals, such as endorphins. The mixed reality environment may be a combination of a virtual environment (e.g. a virtual reality environment) and tangible elements, for example, that may provide a stimulus to a human body or a portion of a human body. In one example, the human senses stimulator device 106 may be used to provide certain tangible stimulus (e.g. heat, smell, pressure, cold, sound, a digital visualization) that acts on one or more senses of the plurality of human senses (5 senses) as a part of the digital therapeutic environment 116, such as audio-visual environment created by the robotic system 104. In another example, the robotic system 104 may be configured to generate a magnetic field at different frequency as a part of the digital therapeutic environment 116.

The communication network 118 may include a medium through which the various devices in the network environment, such as the server arrangement 102, the robotic system 104, the human senses stimulator device 106, the plurality of sensors 108, the communication device 110, the user device 128 of the health care provider 112, and the plurality of different medical equipment 114, may communicate with each other. In some embodiments, a secured and dedicated communication channel may be established between the robotic system 104 and the server arrangement 102. The communication network 118 may be implemented by use of various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), ZigBee, EDGE, IEEE 802.11, light fidelity (Li-Fi), 802.16, IEEE 802.11s, IEEE 802.11g, multi-hop communication, wireless access point (AP), device to device communication, cellular communication protocols, or Bluetooth (BT) communication protocols, or a combination and/or variants thereof. Other examples of the communication network 106 may include, but are not limited to, the Internet, a cloud network, a Long Term Evolution (LTE) network, a secured Wireless Local Area Network (WLAN), a Local Area Network (LAN), a telephone line (POTS), or other wired or wireless network.

The first AI-based system 120 includes suitable circuitry, interfaces, and/or logic configured to be train one or more neural network models, for example, recurrent neural network (RNN), such as Long Short Term Memory networks (LSTM) networks, convolution neural network (CNN), deep neural network (DNN), or an artificial neural network that may be a combination of the RNN and CNN networks. For example, the first AI-based system 120 may be trained to find a relationship among the plurality of different medical diagnosis tests for each user of the plurality of users 130A, 130B, . . . , 130N based on the input of the input-output data pair of each user of the plurality of users 130A, 130B, . . . , 130N. In accordance with an embodiment, the trained model(s) is then deployed in one or more components of the robotic system 104, such as the second AI-based system 126. The deployed pre-trained neural network model(s) is remotely updatable as and when required. In some embodiments, the server arrangement 102 may establish a dedicated and secured link, via the communication network 118 or by use of the communication device 110 (e.g. a 5G enabled repeater device) to update various programmable components, such as the deployed pre-trained neural network model, of the robotic system 104. In an embodiment, the first AI-based system 120 may employ a supervised or unsupervised learning model. The first AI-based system 120 may employ machine learning algorithms, such as supervised, unsupervised, semi-supervised, or reinforcement machine learning algorithms for operation thereof. Typically, the machine learning algorithms refer to a category of algorithms employed by a system that allows the system to become more accurate in predicting outcomes and/or performing tasks, without being explicitly programmed.

The user activities database system 122 comprises suitable logic, circuitry, and interfaces configured to store tracked daily activities of each user of the plurality of users 130A, 130B, . . . , 130N in a specified format. The user activities database system 122 stores different user activities tracked over time for each user who is provided a unique user identity (ID). Each activity may be timestamped based on an occurrence of an event in real-world.

The control circuitry 124 comprises suitable logic, circuitry, and interfaces configured to process sensor data acquired from the plurality of sensors 108. The control circuitry 124 may be further configured to process data of each medical diagnosis test of the plurality of different medical diagnosis tests conducted for each user of the plurality of users 130A, 130B, . . . , 130N. Examples of the control circuitry 124 include an Application-Specific Integrated Circuit (ASIC) processor, a Complex Instruction Set Computing (CISC) processor, a combination of a central processing unit (CPU) and a graphics processing unit (GPU), a microcontroller, and/or other hardware processors.

In operation, there may be a training phase and an operational phase of the personalized health maintenance system 100. In the training phase, the plurality of sensors 108 may be configured to track daily activities of each user of the plurality of users 130A, 130B, . . . , 130N. Typically, each human being is different and reacts differently to a medicine. For example, a first user 130A suffering from a disease may be responsive to a small dosage of a first medicine whereas a second user 130B may require a comparatively higher dosage to induce a similar response. Alternatively, the first user 130A suffering from the disease may require a high dosage of a second medicine whereas the second user 130B may require a comparatively less dosage of the second medicine to induce a similar response. Currently, doctors utilize or employ a trial and error method to find right medicine and dosage for an individual. Such difference may be due to variability in genome and other environmental factors. There may be other situations like trauma in the past, difference in user activities or user habits (e.g. difference sleeping pattern, amount of physical activities per day, food eating habits, general temperament, user behaviour, seating posture, walking posture etc) that may indicate how likely a user may have a medical condition, and the type of medical condition. For example, a user who may regularly be seated for long hours in a wrong seating posture, may likely be prone to backache or musculoskeletal diseases. Thus, tracking of user activities provides not only provides an early signal to a medical condition, but may also help during treatment of a disease. In other words, an accurate knowledge of which activities led to a particular medical condition, may be a useful cue in a later stage when the cause of the medical condition is determined.

In accordance with an embodiment, the plurality of sensors 108 may be configured to communicate the sensor data of a user, such as the first user 130A, to the server arrangement 102. Moreover, users, for example, the first user 130A may undergo regular health check-up to know about their health. Alternatively, whenever the first user 130A suffers from a certain medical condition, the first user 130A may visit different health care providers, such as the health care provider 112, to undergo several diagnostic tests as prescribed by a physician. Thus, during a lifetime of an individual, the first user 130A may undergo several medical diagnostic tests. In an example, the plurality of different medical diagnosis tests may include a genetic test, a psychological test, a laboratory based medical diagnosis test, and a non-laboratory based medical diagnosis test (for example, blood glucose, blood pressure, stress level etc. can be measured by the first user 130A using various ready-to-use kits and devices from the comfort of home). The plurality of different medical diagnosis tests may be conducted from the plurality of different medical equipment 114 that output test results in different data formats. Such test results including the input sample details may be communicated to the server arrangement 102 each time such test(s) is/are conducted.

The control circuitry 124 may be configured to read an input-output data pair of each medical diagnosis test of the plurality of different medical diagnosis tests conducted for the first user 130A. The control circuitry 124 may be further configured to convert the input-output data pair of the plurality of different medical diagnosis tests into an AI system-readable data format. The AI system-readable data format may be a common format that may be fed as input to the first AI-based system 120. Moreover, the document type of some of the medical diagnosis test of the plurality of different medical diagnosis tests, may be different. For example, the diagnostic result of blood glucose may have an input field (such as blood drop), and output field (such as a blood glucose value) along with a unique patient identity, a time of day, temperature, and other accessory information, for example, fasting blood sugar to non-fasting blood sugar etc. However, a CT-scan or an X-ray result is much different and difficult to analyse automatically by a machine. Similarly, the input and output format and requirements are typically different for the plurality of plurality of different medical diagnosis tests. The server arrangement 102 may have configurable plugins (i.e. a plurality of different software application modules suitable to detect and process at least one type of medical diagnosis tests). The control circuitry 124 may be further configured to select an appropriate software application module from the plurality of different software application modules to process one type of diagnostic results. For example, image processing module may be used to process the X-ray result. All the input of medical diagnosis tests results may be converted to a common format that may be easily read by the first AI-based system 120. In an example, the AI system-readable data format may include patient information (e.g. patient unique identity), data and time information when the test was conducted, a plurality of data fields, and corresponding measured values.

The control circuitry 124 may be further configured to cross-correlate a plurality of results of each medical diagnosis test of the plurality of different medical diagnosis tests to find a relationship among the plurality of different medical diagnosis tests for the first user 130A, based on an input of the input-output data pair in the AI system-readable data format. The control circuitry 124 may be further configured to retrieve genomic information of the first user 130A. For example, deoxyribonucleic acid (DNA) or exome only sequencing may be performed by use of the DNA sequencer using known sequencing technologies, such as next-generation sequencing (NGS). The genomic information (e.g. DNA sequence) may be aligned with a reference genome (e.g. human genome assembly, hg38) and other gene variant sequences to find presence of different mutations, such as copy number variants (CNVs), indels, single nucleotide variant (SNVs), and other variants that are known to cause diseases or disorder. The genomic information and the presence of such mutations in the genomic information for the first user 130A may be stored in a database in the server arrangement 102. The genomic information and the presence of such mutations in the genomic information may be further cross-related with the plurality of results of each medical diagnosis test of the plurality of different medical diagnosis tests. Additionally, a pharmacogenomics analysis may be performed to find a relation between effect of medicine and genes as well as the mutations present in the genomic information of the first user 130A. The control circuitry 124 may be further configured to determine if a pattern exists in the plurality of results of each medical diagnosis test of the plurality of different medical diagnosis tests of the first user 130A. Additionally, the control circuitry 124 may be further configured to determine if a pattern exists in the plurality of results of plurality of different medical diagnosis tests as well the genomic information of the first user 130A.

In accordance with an embodiment, the first AI-based system 120 may be configured to utilize unsupervised learning to find the relationship among the plurality of different medical diagnosis tests (including genomic information) for each user of the plurality of users 130A, 130B, . . . , 130N in the training phase. In the unsupervised learning, a neural network schema of the first AI-based system 120 may be provided with unlabeled, uncategorized data of the input-output data pair in the AI system-readable data format and the first AI-based system 120 act on the data without prior training. In other words, the unsupervised learning may be a deep learning model that handle the input of the input-output data pair in the AI system-readable data format without explicit instructions, and then the neural network schema of the first AI-based system 120 attempts to automatically find structure and pattern in the input-output data pair by extracting features and analyzing its pattern to draw inferences. In some embodiments, in the training phase, the first AI-based system 120 may be trained by supervised learning. In an example, the first AI-based system 120 may be configured to cross-correlate input sample and results of different medical diagnosis tests, such as X-rays, mammogram, genetic screening test, MRI, blood tests, etc., conducted from the plurality of different medical equipment 114. The first AI-based system 120 may be configured to find relationship among those tests for one individual or a group of individuals and learn from it. The control circuitry 124 may be configured to determine a coherent health state of each user of the plurality of users 130A, 130B, . . . , 130N, based on the cross-correlation of the plurality of different medical diagnosis tests (that may include genetic test).

The control circuitry 124 may be further configured to utilize tracked daily activities for each user of the plurality of users 130A, 130B, . . . , 130N. The control circuitry 124 may be configured to determine a plurality of candidate cause-result pairs for the determined coherent health state of each user of the plurality of users 130A, 130B, . . . , 130N, based on an association of the set of user activities of each corresponding user of the plurality of users 130A, 130B, . . . , 130N with the cross-correlation of the plurality of results of the plurality of different medical diagnosis tests for each user of the plurality of 130A, 130B, . . . , 130N. For example, if the result is diabetes, possible causes specific to each user of the plurality of 130A, 130B, . . . , 130N, may be found from the plurality of different medical diagnosis tests as well as the historical analysis of the set of user activities for each user. It may be determined whether a user had poor eating habits, poor physical activity, or a sudden rise in stress levels due to an event, for better understanding of the disease for each user. In some users, the reason or causes may be different, for example, genetic or parents having diabetes or excessive smoking combined with excessive carbohydrate intake, and the like.

In accordance with an embodiment, the control circuitry 124 may be further configured to calibrate the cross-correlation of the plurality of results of the plurality of different medical diagnosis tests for each user of the plurality of users 130A, 130B, . . . , 130N. The weights of the first AI-based system 120 may be adjusted accordingly so that the output is more accurate next time. The calibration may be executed based on the determined plurality of candidate cause-result pairs for the determined coherent health state and a feedback from the output of the first AI-based system 120.

In accordance with an embodiment, the control circuitry 124 may be further configured to predict a plurality of digital therapeutic environments based on the determined coherent health state of each user of the plurality of users 130A, 130B, . . . , 130N. The control circuitry 124 may be configured to determine a plurality of impact scores for a plurality of predicted digital therapeutic environments based on the determined coherent health state of each user of the plurality of users 130A, 130B, . . . , 130N and the determined plurality of candidate cause-result pairs. The first-AI system 120 may predict what is a likelihood of effectiveness of each predicted digital therapeutic environment of the predicted plurality of digital therapeutic environments. The prediction and impact scores may be different for different users based on their own unique characteristics, such as tracked user activities, differences in genes, exposure to pollution, any specific event, and environment factors.

The robotic system 104 may be configured to output the digital therapeutic environment 116 around selected users (e.g. both specifically and randomly selected sample users) for the training phase, for example, a first set of users from the plurality of users 130A, 130B, . . . , 130N. The digital therapeutic environment 116 may be a human-sense stimulating mixed reality environment that induces a specific stimulus to each user of the first set of users for remediation of a same medical condition of the determined coherent health state of each user of the first set of users. The same medical condition and different effect on different users indicates variability in users and facilitates the first AI-based system 120 to learn the reasons for variations (including variation due to genomic information or mutations present in the genomic information). In accordance with an embodiment, the control circuitry 124 may be further configured to determine a response to the specific stimulus provided by the output of the digital therapeutic environment 116 around each selected user of the first set of users. Thus, the neural network schema of the first AI-based system 120 may be further tuned to find relationships among cause/symptoms, effects, and how an individual is responding to medicines or the outputted digital therapeutic environment 116. All these information pieces (i.e. relationships) may be grouped and then sub-grouped and a learning may be derived. For example, it may be found if there exists a correlation, or no correlation, or less correlation among the selected diagnosis tests and analysed information. Further, the process of tagging and elimination for each data point may be executed to identify correct correlation, inferences, and response(s) to provided stimulus, based on continuous training. Thus, a trained model (i.e. a trained first AI-based system 120) may be obtained. Thus, different therapies, such as different predicted digital therapeutic environments, are electronically evaluated by the trained first AI-based system 120, where the most effective digital therapeutic environment is selected and further adaptively finetuned over a time period by the robotic system 104.

In the operational phase, the learnings of the trained first AI-based system 120 may be used to update the second AI-based system 126, by a transfer-learning process. For example, the calibrated weights (or probabilities) may be communicated from the server arrangement 102 to the robotic system 104. In some embodiments, the trained first AI-based system 120 may be used for deployment into a new robotic system, such as the robotic system 104. The first AI-based system 120 may function as a main AI and the second AI-based system 126 may function as a local AI, which may be updated as and when required by the first AI-based system 120. The second AI-based system 126 may be computationally lighter (e.g. having a smaller number of hidden layers as compared to the first AI-based system 120).

In accordance with an embodiment, a new user may be diagnosed with a medical condition, which may require a treatment or may be undergoing a treatment and may be consuming certain medicines. In such a case, the personalized health maintenance system 100 may be used to complement and improve the existing model of treatments (e.g. by medicines) by reduction in the usage and dosage of medicines, and thereby also reducing the side effects of medicines. The personalized health maintenance system 100 may be used as an alternative form of treatment the medical condition without the need of taking medicines or at least reducing the intake or dosage of medicines.

In accordance with an embodiment, in the operational phase, the control circuitry 124 may be configured to read an input-output data pair of each medical diagnosis test of a plurality of different medical diagnosis tests conducted for a new user (e.g. the first user 130A). The control circuitry 124 may be further configured to convert the input-output data pair of the plurality of different medical diagnosis tests into an AI system-readable data format. The control circuitry 124 may be further configured to cross-correlate a plurality of results of each medical diagnosis test of the plurality of different medical diagnosis tests to find a relationship among the plurality of different medical diagnosis tests for the new user, based on an input of the input-output data pair in the AI system-readable data format. Additionally, the control circuitry 124 may be further configured to determine if a pattern exists in the plurality of results of plurality of different medical diagnosis tests as well the genomic information of the new user. The control circuitry 124 may be further configured to determine a coherent health state of the new user based on the cross-correlation of the plurality of different medical diagnosis tests (which may include the genetic test). The control circuitry 124 may be further configured to extract a plurality of dataset related to the new user from the user activities database system 122. The plurality of dataset comprises tracked daily activities for a plurality of specific timelines that precedes a date and a timepoint on which each medical diagnosis test of the plurality of different medical diagnosis text is conducted. The control circuitry 124 may be further configured to determine a plurality of candidate cause-result pairs for the determined coherent health state of the new user based on an association of a set of user activities in the extracted plurality of dataset with the cross-correlation of the plurality of results of the plurality of different medical diagnosis tests for the new user. The control circuitry 124 may be further configured to determine a plurality of impact scores for a plurality of predicted digital therapeutic environments based on the determined coherent health state of the first user and the determined plurality of candidate cause-result pairs.

The robotic system 104 may then output, under control of the second AI-based system 126 and the first AI-based system 120, a first digital therapeutic environment around the new user based on a predicted digital therapeutic environment associated with a highest impact score from the plurality of impact scores. The first digital therapeutic environment may be a human sense stimulating mixed reality environment that induces a specific stimulus to the new user for remediation of at least one condition of the determined coherent health state of the new user. The robotic system 104 may be configured to determine which medicine, or which digital therapeutic environment, or a specific combination of different therapies (i.e. physical therapy, digital therapeutic environment, and gene therapy), medicine dosages, works best (i.e. provides a health score above a set health threshold value, for example, 95). The heath score refers to a cumulative heath score generated based on a comparison between current measured heath parameters from the plurality of different diagnostic tests against normal parameters of a healthy individual. A unified decision support information may be generated that provides fine-tuned or calibrated treatment plan having evidence of specific medicines, digital therapeutic environment, or a combination of different therapies (i.e. physical therapy, digital therapeutic environment, and gene therapy), and medicine dosages, which are most effective for the new user to derive a desired response.

In an example, the most effective digital therapeutic environment may be a mindfulness therapy. The mindfulness therapy refers to a therapy to engage a given user so that mind is not pre-occupied and the senses of the given user function in the now/present. The digital therapeutic environment may be a virtual reality environment (or mixed reality environment) created to engage the new user in the present, where the new user is aware of what one is doing and is able to focus on a specific task. Thus, the robotic system 104 may be used to train people to be aware of the present and be engaged (i.e. to focus on a task or idea). The digital therapeutic environment may constantly challenge a human mind to learn new skills and enhance social behavior. Further, there are certain medicines that are used to controls behavior, for example, attention deficit hyperactivity disorder (ADHD) is controlled by a medicine. Such digital therapeutic environment created may then eliminate or at least reduce the need for such medicines.

In accordance with an embodiment, the control circuitry 124 may be further configured to determine whether an alteration is required in a first set of dosages of a first set of medicines prescribed for the at least one condition of the determined coherent health state of the new user, based on the determined response to the specific stimulus provided by the output of the first digital therapeutic environment around the new user. The control circuitry 124 may be further configured to determine a second set of dosages for the first set of medicines that is different from the first set of dosages based on the determined response to the specific stimulus. The control circuitry 124 may be further configured to communicate a medicine dosage change recommendation report for the new user to a prespecified user device (e.g. the user device 128) of the health care provider 112. The medicine dosage change recommendation report may include the second set of dosages for the first set of medicines and a plurality of health indicators related to the determined response to the specific stimulus provided by the output of the first digital therapeutic environment. Such medicine dosage change recommendation report may assist a physician to make an informed decision to precisely reduce the first set of dosages of the first set of medicines approximately to the recommended second set of dosages.

In accordance with an embodiment, the control circuitry 124 may be further configured to predict a sequence of digital therapeutic environments and a time schedule in accordance to which each digital therapeutic environment of the sequence of digital therapeutic environments is to be applied on the new user, based on the determined coherent health state of the new user and the determined plurality of candidate cause-result pairs.

In accordance with an embodiment, the robotic system 104 may be further configured to output, under control of the second AI-based system 126 and/or the trained first AI-based system 120, the predicted sequence of digital therapeutic environments in accordance to the time schedule and a current health state specific to the new user. The outputted sequence of digital therapeutic environments may induce a series of different stimuli specific to the new user for remediation of at least one condition of the determined coherent health state of the new user. In accordance with an embodiment, the robotic system 104 may communicate a control signal to the human senses stimulator device 106 during the output of the first digital therapeutic environment or during the output of the predicted sequence of digital therapeutic environments. The human senses stimulator device 106 may be configured to generate a single sense stimulating output to stimulate a specific sense of a plurality of human sense based on a type of control signal received from the robotic system 104. In some embodiments, based on the type of control signal received from the robotic system 104, the human senses stimulator device 106 may be configured to generate a multi-sense stimulating output to concurrently stimulate at least two senses of the plurality of human senses. For example, the sense of smell and heat sensation to a specific body portion may be stimulated (or applied), which in turn may induce a stimulus resulting in acceleration of the release of well-being chemicals, e.g. endorphins.

In accordance with an embodiment, the robotic system 104 may be further configured to communicate a stimulation request pack to the human senses stimulator device 106 to control the human senses stimulator device 106 to contribute at the output of the first digital therapeutic environment. The stimulation request pack may include the type of control signal for the single sense stimulating output or the multi-sense stimulating output, a time schedule that defines a specific activation time and a specific duration to generate output, an intensity of output, and a set of sense identifiers. Each sense identifier of the set of sense identifiers may indicate a unique specific sense stimulating item to be selected for output in accordance with the time schedule. For example, a first sense identifier may indicate a specific smell for output. In such a case, the intensity of output defines what amount of liquid or gas to be sprayed and in which direction.

Figure 2:
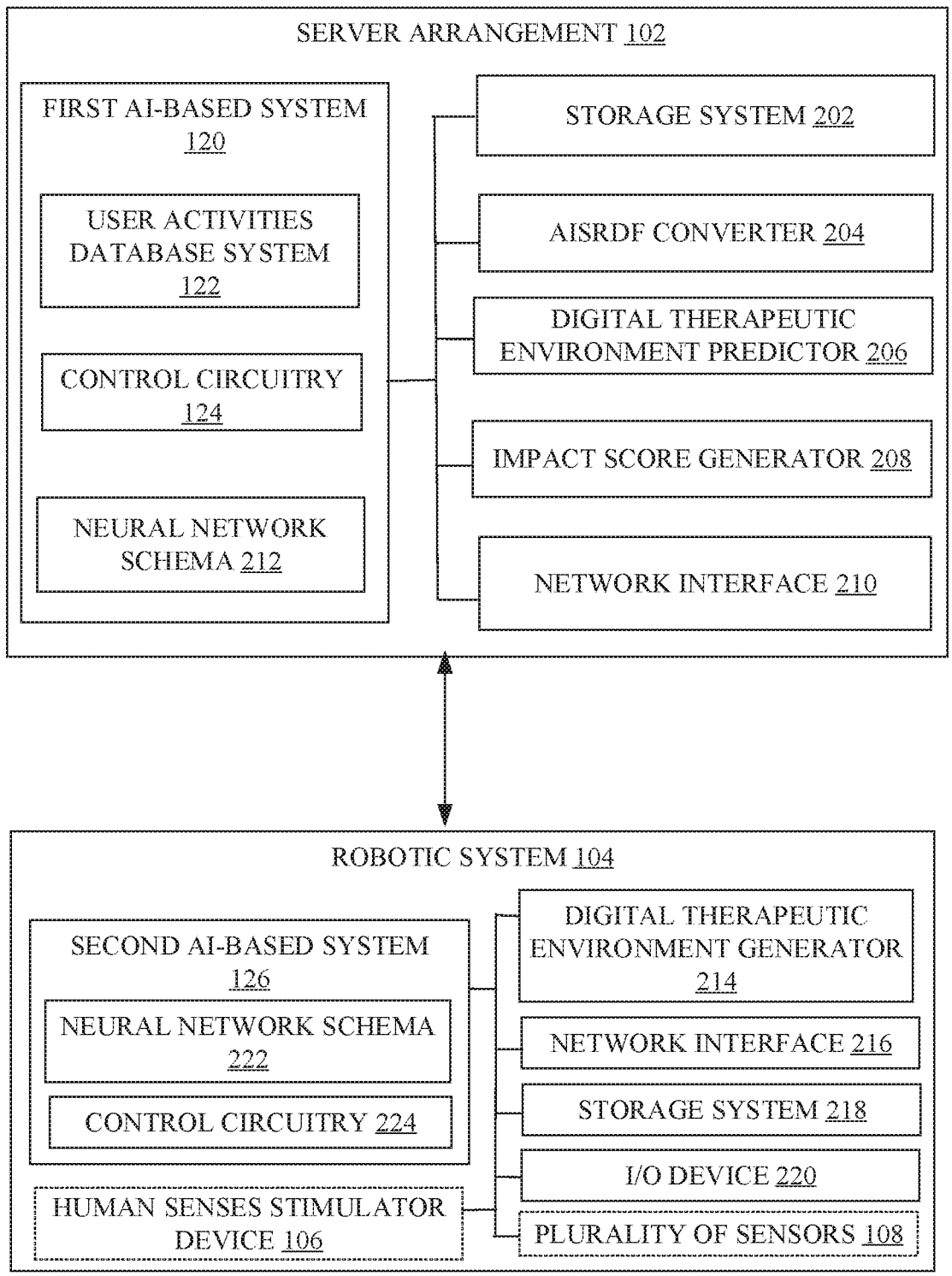
FIG. 2 illustrates different components of a server arrangement and a robotic system of the personalized health maintenance system of FIG. 1, in accordance with an exemplary embodiment of the disclosure.

FIG. 2 illustrates different components of a server arrangement and a robotic system of the personalized health maintenance system of FIG. 1, in accordance with an exemplary embodiment of the disclosure. FIG. 2 is described in conjunction with elements from FIG. 1. With reference to FIG. 2, there is shown the server arrangement 102 and the robotic system 104 of the personalized health maintenance system 100 (of FIG. 1). The server arrangement 102 may further include a storage system 202, an Artificial Intelligence System-Readable Data Format (AISRDF) converter 204, a digital therapeutic environment predictor 206, an impact score generator 208, and a network interface 210. The first AI-based system 120 may include the user activities database system 122, the control circuitry 124, and a neural network schema 212. The robotic system 104 may further include a digital therapeutic environment generator 214, a network interface 216, a storage system 218, and an Input/Output (I/O) device 220. The second AI-based system 126 of the robotic system 104 may include a neural network schema 222 and control circuitry 224.

The storage system 202 may comprise suitable logic, circuitry, and/or interfaces that may be configured to temporarily store health information (for processing) acquired form the plurality of different medical equipment 114. The storage system 202 may be further configured to temporarily store user activities information acquired from the plurality of sensors 108. In accordance with an embodiment, the storage system 202 may be temporary storage system. The storage system 202 may also store instructions executable by the control circuitry 124. Examples of implementation of the storage system 202 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The AISRDF converter 204 may comprise suitable logic, circuitry, interfaces, and/or code that may be configured to convert the input-output data pair for the plurality of different medical diagnosis tests into an AI system-readable data format (AISRDF). Examples of implementations of the AISRDF converter 204 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other control circuits.

The digital therapeutic environment predictor 206 may comprise suitable logic, circuitry, interfaces, and/or code that may be configured to predict a plurality of digital therapeutic environments based on the determined coherent health state each user of the plurality of users 130A, 130B, . . . , 130N and the determined plurality of candidate cause-result pairs. Examples of implementations of the AISRDF converter 204 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other control circuits.

The impact score generator 208 may comprise suitable logic, circuitry, interfaces, and/or code that may be configured to determine a plurality of impact scores for the plurality of predicted digital therapeutic environments based on the determined coherent health state of each user of the plurality of users 130A, 130B, . . . , 130N and the determined plurality of candidate cause-result pairs. Examples of implementations of the AISRDF converter 204 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other control circuits.

The network interface 210 may comprise suitable logic, circuitry, interfaces, and/or code that may be configured to connect and communicate with a plurality of devices in the network environment of the personalized health maintenance system 100. The network interface 210 may implement known technologies to support wireless communication. The network interface 210 may include, but are not limited to an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer. The network interface 210 may communicate via offline and online wireless communication with networks, such as the Internet, an Intranet, and/or a wireless network, such as a cellular telephone network, a wireless local area network (WLAN), personal area network, and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), LTE 4G, 5G, time division multiple access (TDMA), Bluetooth, Wireless Fidelity (Wi-Fi) (such as IEEE 802.11, IEEE 802.11b, IEEE 802.11g, IEEE 802.11n, and/or any other IEEE 802.11 protocol), voice over Internet Protocol (VoIP), Wi-MAX, Internet-of-Things (IoT) technology, Machine-Type-Communication (MTC) technology, a protocol for email, instant messaging, and/or Short Message Service (SMS).

The neural network schema 212 may refer to a neural network architecture having a number of layers, such as an input layer, an output layer, and intermediate layers that operates on data received at the input layer to generate corresponding output at the output layer. The neural network schema 212 may also be referred to as a neural network model. The neural network schema 212 of the first AI-based system 120 may be provided with unlabeled, uncategorized data of the input-output data pair in the AI system-readable data format and the first AI-based system 120 act on the data to automatically find structure and pattern in the input-output data pair by extracting features and analyzing its pattern to draw inferences.

The digital therapeutic environment generator 214 may comprise suitable logic, circuitry, interfaces, and/or code that may be configured to output a customized digital therapeutic environment (e.g. the digital therapeutic environment 116) around a user. The digital therapeutic environment generator 214 may control output of the customized digital therapeutic environment by use of various modules and devices, of the personalized health maintenance system 100. Examples of implementations of the digital therapeutic environment generator 214 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), a specialized hardware generator, and/or other control circuits.

The network interface 216 may comprise suitable logic, circuitry, interfaces, and/or code that may be configured to connect and communicate with a plurality of devices in the network environment of the personalized health maintenance system 100. The network interface 216 may be similar to that of the network interface 210.

The storage system 218 may comprise suitable logic, circuitry, and/or interfaces that may be configured to store health information acquired from the plurality of different medical equipment 114. The storage system 202 may be further configured to store user activities information acquired from the plurality of sensors 108. The storage system 218 may be used for temporary storage or persistent storage.

The I/O device 220 may comprise suitable logic, circuitry, interfaces, and/or code that may be configured to receive an input from the one or more users. The I/O device 220 may be further configured to provide an output to the one or more users. The I/O device 220 may comprise various input and output devices that may be operable to communicate with the control circuitry 224. Examples of the input devices may include, but are not limited to, a touch screen, physical input buttons, a joystick, a microphone, and/or a docking station. Examples of the output devices may include, but are not limited to, an-inbuilt display screen, a touch screen display, and/or a speaker.

The neural network schema 222 of the second AI-based system 126 of the robotic system 104 may be similar to that of the neural network schema 212 of the server arrangement 102. This enables transfer learning from the first AI-based system 120 to the second AI-based system 126, and vice-versa.

The control circuitry 224 of the robotic system 104 comprises suitable logic, circuitry, and interfaces configured to process sensor data acquired from the plurality of sensors 108. The control circuitry 224 may be communicatively coupled to the digital therapeutic environment generator 214, the network interface 216, the storage system 218, the I/O device 220, the second AI-based system 126, and the first AI-based system 120. Examples of the control circuitry 224 include an Application-Specific Integrated Circuit (ASIC) processor, a Complex Instruction Set Computing (CISC) processor, a combination of a central processing unit (CPU) and a graphics processing unit (GPU), a microcontroller, and/or other hardware processors.

Figure 3:
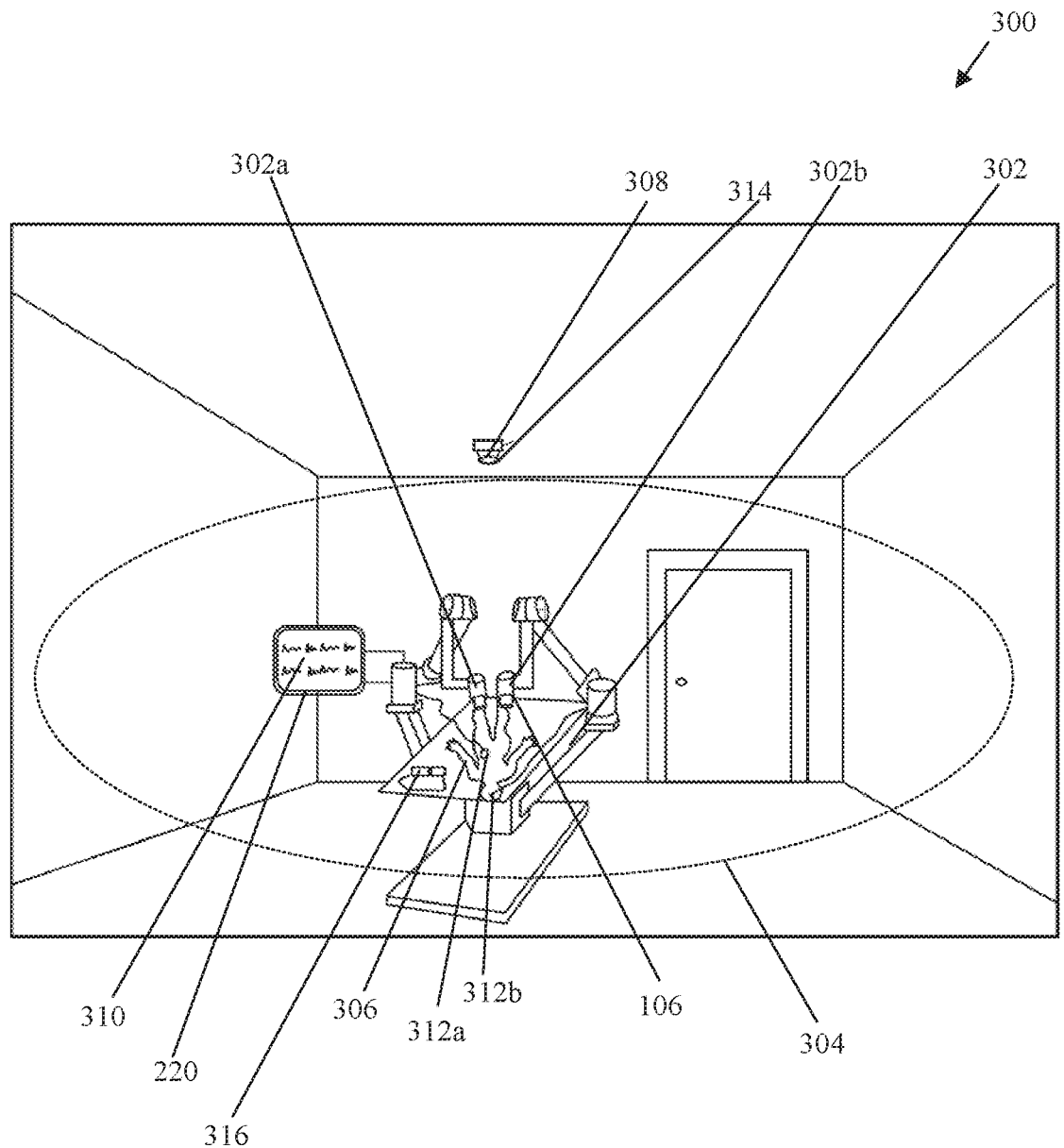
FIG. 3 illustrates an exemplary scenario for implementation of the personalized health maintenance system, in accordance with an exemplary embodiment of the disclosure.
Figure 4A:
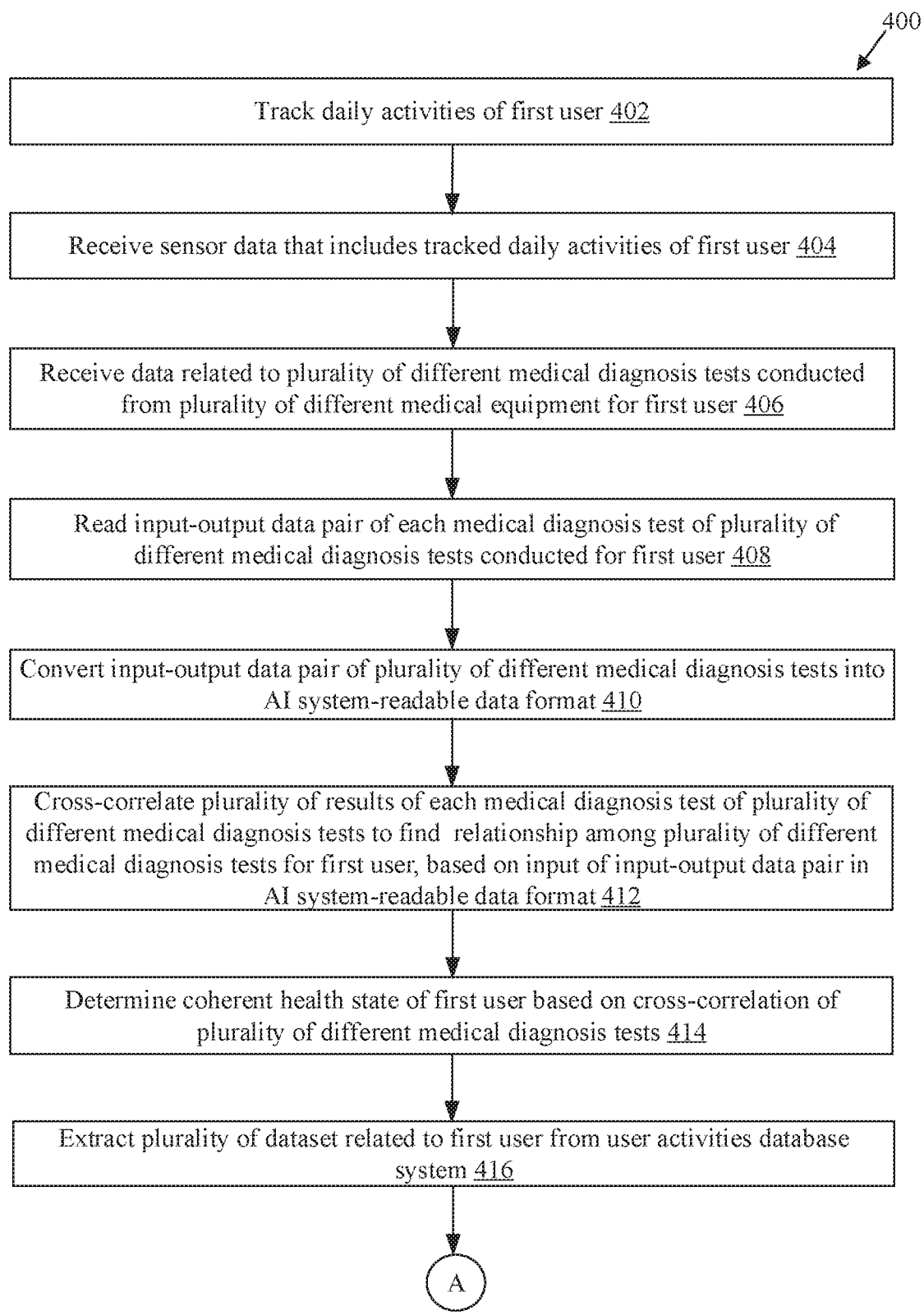
FIGS. 4A, 4B, 4C, and 4D collectively, illustrate a method for personalized health maintenance, in accordance with an exemplary embodiment of the disclosure.
Figure 4B:
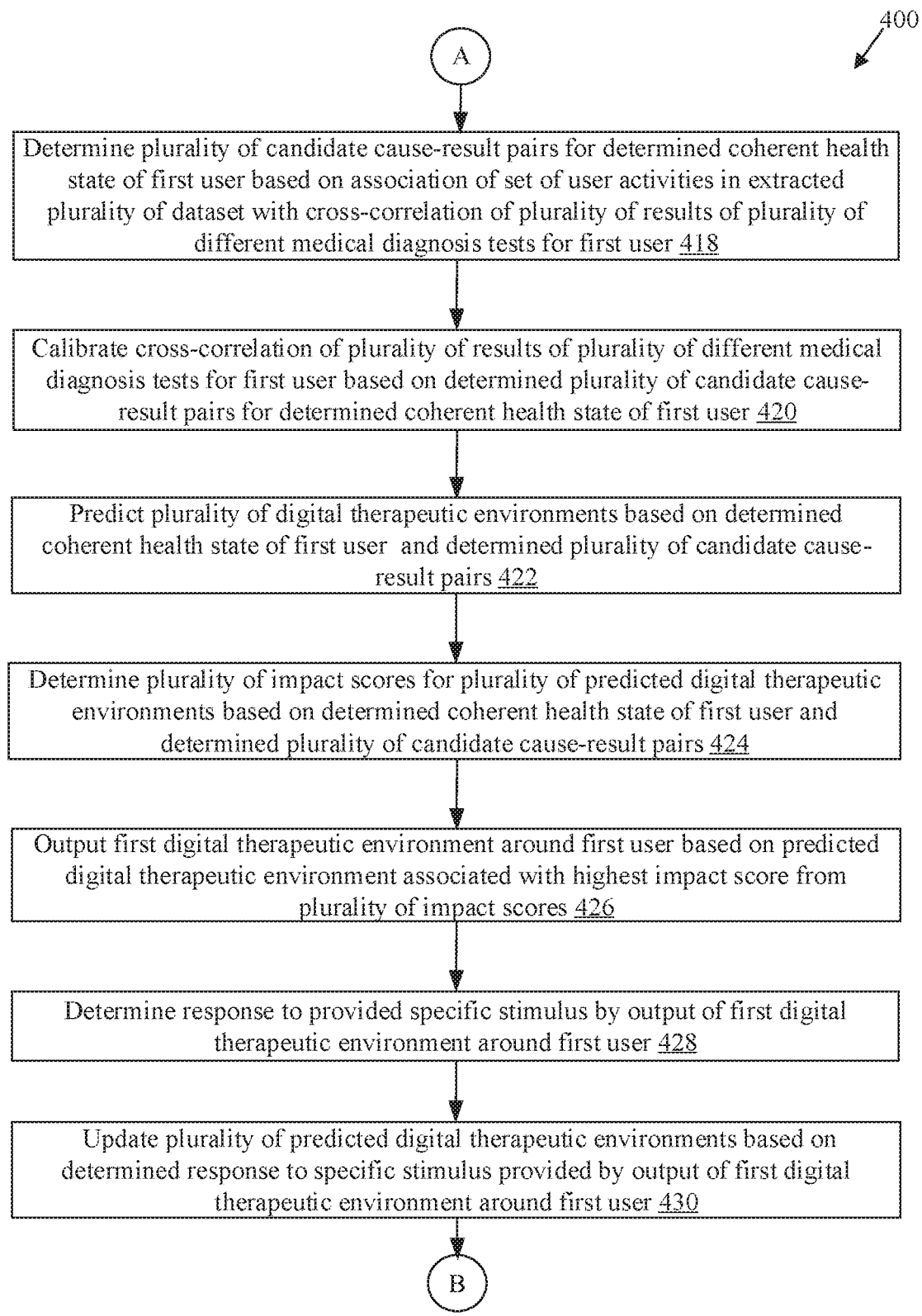
Figure 4C:
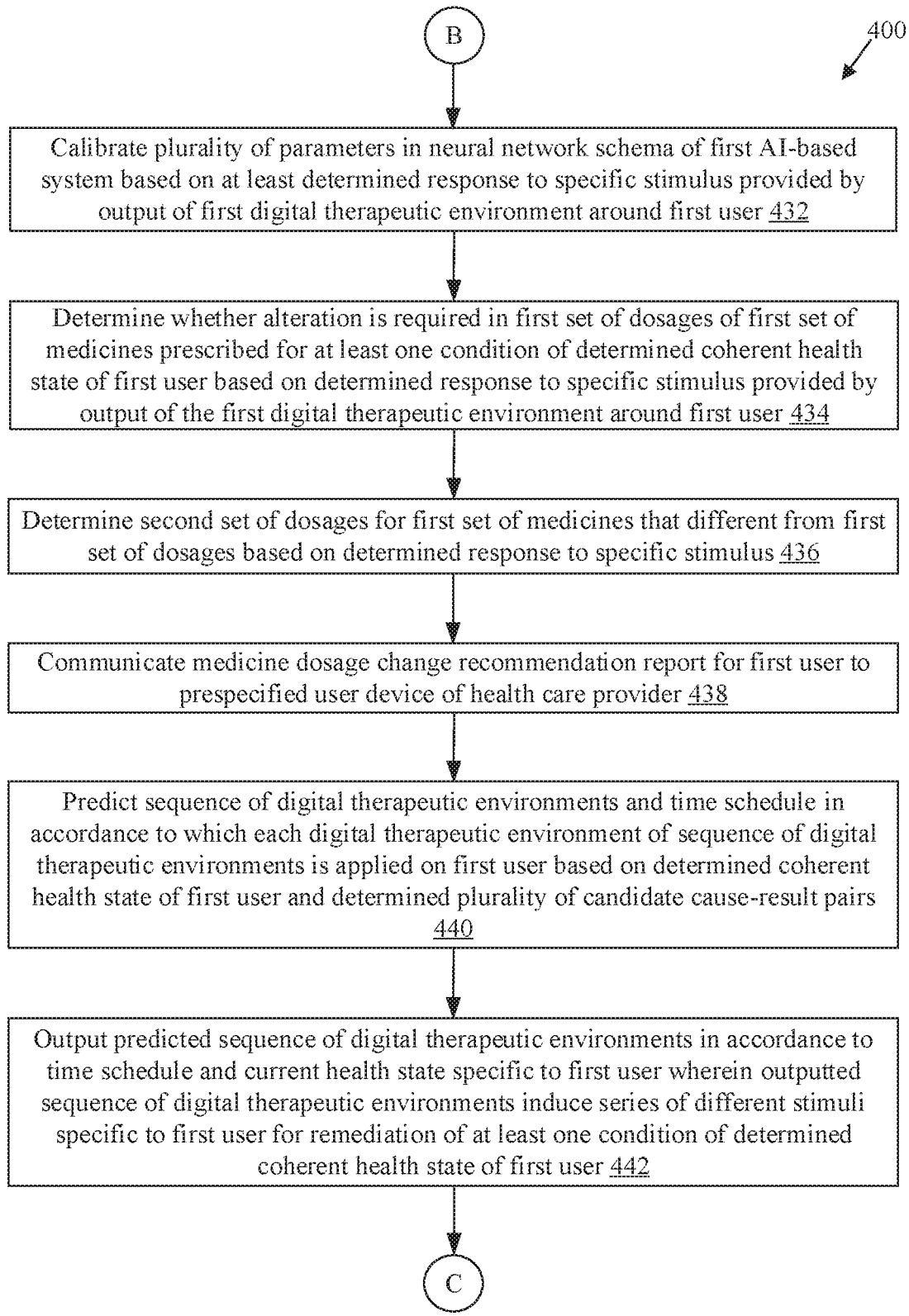
Figure 4D:
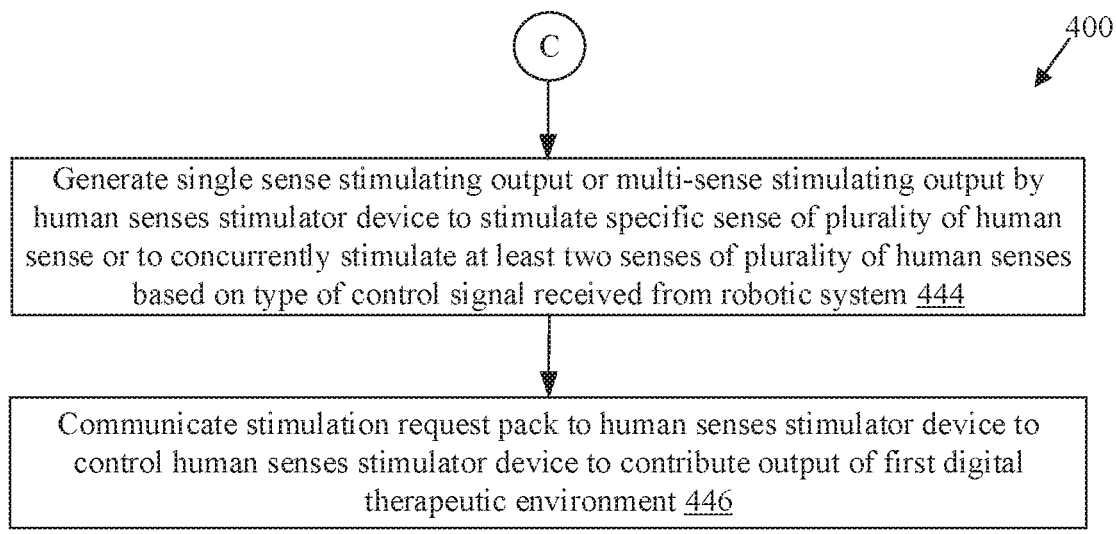

FIG. 3 illustrates an exemplary scenario for implementation of the personalized health maintenance system, in accordance with an exemplary embodiment of the disclosure. FIG. 3 is described in conjunction with elements from FIGS. 1 to 2. With reference to FIG. 3, there is shown an exemplary scenario 300 that depicts a robotic system 302 configured to output a first digital therapeutic environment 304 for a subject 306. In an example, the subject 306 may be a sportsman, a student, a patient, or any person who intend to improve his performance or cognitive abilities. The robotic system 302, the first digital therapeutic environment 304, and the subject 306 may correspond to the robotic system 104, the digital therapeutic environment 116, and the first user 130A, respectively (of FIG. 1). The robotic system 302 may be communicatively coupled with the server arrangement 102.

In accordance with the exemplary scenario 300, the robotic system 302 may include two arms 302a and 302b. The first arm 302a may be equipped with a device to generate a magnetic field at different frequency and further to monitor body of the subject 306 or the reflexes of the subject 306. The second arm 302b may be equipped with the human sense stimulator device 106. The two arms 302a and 302b may be movable arms to direct corresponding output from the devices provided therein to specific body areas of the subject 306. There is further shown a 360-degree projector, hereinafter referred to as a projector 308 communicatively coupled to the robotic system 302 (by wired or wireless medium). The robotic system 302 may further include the I/O device 220 that has a user interface 310 rendered thereon. The user interface 310 may be used to receive an input from a user (e.g. the subject 306 or a health care professional). This may be to initiate the provisioning of a multi-modal therapy, to change a setting of the robotic system 302, or to test run the robotic system 302. The robotic system 302 may further include, for example, two internal response sensors 312a and 312b that may be attached to the body of the subject 306 in a non-invasive manner. The robotic system 104 further includes an imaging device 314 (i.e., an external response sensor) that may be configured to obtain one or more images of the subject 306 when the subject 306 undergoes the multi-modal therapy by the robotic system 302. The one or more images or a video may be indicative of facial expressions and gestures of the subject 306. There is further shown a virtual reality headset 316 communicatively coupled to the robotic system 302 (wired or wirelessly).

The robotic system 302 may be configured to output the first digital therapeutic environment 304 under the control of the first AI-based system 120 and the second AI-based system 126. The first digital therapeutic environment 304 may be a human-sense stimulating mixed reality environment that induces a specific stimulus to the subject 306 for remediation of at least one condition of the determined coherent health state of the subject 306.

In accordance with an embodiment, the first digital therapeutic environment 304 may keep the subject 306 engaged and enhance the level of release of the well-being chemicals, such as endorphins, or specific hormone within the subject 306. This may increase a person's learning ability, concentration, and focus. For example, based on personalized tracking of daily activities of the subject 306, the first AI-based system 120 may learn that a specific music or a category of music is responsible for reducing stress for the subject 306. Thus, an audio environment may be generated by the human sense stimulator device 106. In another example, based on the cross-correlation of a plurality of results of each medical diagnosis test of the plurality of different medical diagnosis tests, the first AI-based system 120 may be configured to find a relationship among the plurality of different medical diagnosis tests for the subject 306. Further, the first AI-based system 120 may be configured to determine a coherent health state of the subject 306 based on the cross-correlation of the plurality of different medical diagnosis tests. For example, the first AI-based system 120 may be further configured to determine that a specific musculoskeletal portion has an issue with blood circulation. This may be further confirmed based on assessment of causes from the tracked daily activities of the subject 306. The first AI-based system 120 may be further configured to predict a plurality of digital therapeutic environments, and then finally select the best digital therapeutic environment, such as the first digital therapeutic environment 304, to remediate the pain associated with the specific musculoskeletal portion of the subject 306. The best digital therapeutic environment, such as the first digital therapeutic environment 304, may be determined based on a highest impact score of a plurality of impact scores.

In accordance with an embodiment, if in the coherent health state of the subject 306, it is determined that the subject 306 requires improvement in concentration, then a different digital therapeutic environment may be outputted by the robotic system 302. For example, the first AI-based system 120 may learn that a beach area with music of chirping birds increases concentration of the subject 306, then a suitable digital therapeutic environment may be outputted by the robotic system 302. For example, the digital therapeutic environment may include a visualization of a beach area that may be projected by the projector 308 in 360 degree in a physical enclosure, such as room. Alternatively, a virtual reality scene of the beach area may be created by the virtual reality headset 316 under the control of the second AI-based system 126 and/or the first AI-based system 120. At the same time, the music of chirping birds may be outputted by the human sense stimulator device 106. The human sense stimulator device 106 may also output a specific smell to contribute to the effectiveness of increasing concentration. Moreover, the first arm 302a equipped with the device to generate a magnetic field at different frequency, may monitor the reflexes of the subject 306. The robotic system 302 may be configured to determine a response to the specific stimulus provided by the output of the digital therapeutic environment around the subject 306 by use of the two internal response sensors 312a and 312b and the imaging device 314. The second AI-based system 126 and the first AI-based system 120 may continuously learn and improve itself based on the tracking of user activities and measuring the response to provided stimulus, and accordingly the digital therapeutic environment may be updated or changed.

FIGS. 4A, 4B, 4C, and 4D collectively, illustrate a method for personalized health maintenance, in accordance with an exemplary embodiment of the disclosure. FIGS. 4A, 4B, 4C, and 4D are described in conjunction with elements from FIGS. 1 to 3. With reference to FIGS. 4A to 4D, there is shown a flowchart 400 comprising exemplary operations 402 through 446 by the personalized health maintenance system 100.

At 402, daily activities of the first user 130A may be tracked. The plurality of sensors 108 may be configured to track the daily activities of the first user 130A. At 404, sensor data that includes the tracked daily activities of the first user 130A, may be received. The control circuitry 124 may be configured to receive the sensor data that includes the tracked daily activities of the first user 130A.

At 406, data related to a plurality of different medical diagnosis tests conducted from the plurality of different medical equipment 114 for the first user 130A, may be received. The control circuitry 124 may be further configured to receive data related to the plurality of different medical diagnosis tests. The plurality of different medical diagnosis tests may be conducted from the plurality of different medical equipment 114 that output test results in different data formats. The plurality of different medical diagnosis tests may include a genetic test, a psychological test, a laboratory based medical diagnosis test, and/or a non-laboratory based medical diagnosis test. At 408, an input-output data pair of each medical diagnosis test of the plurality of different medical diagnosis tests conducted for the first user 130A may be read. The control circuitry 124 (or control circuitry 224) may be further configured to read the input-output data pair of each medical diagnosis test of the plurality of different medical diagnosis tests.

At 410, the input-output data pair of the plurality of different medical diagnosis tests may be converted into an AI system-readable data format. The AISRDF converter 204 may be configured to convert the input-output data pair of the plurality of different medical diagnosis tests into an AI system-readable data format. At 412, a plurality of results of each medical diagnosis test of the plurality of different medical diagnosis tests may be cross-correlated to find a relationship among the plurality of different medical diagnosis tests for the first user 130A, based on an input of the input-output data pair in the AI system-readable data format. The control circuitry 124 (or control circuitry 224) may be further configured to cross-correlate the plurality of results of each medical diagnosis test of the plurality of different medical diagnosis tests.

At 414, a coherent health state of the first user 130A may be determined based on the cross-correlation of the plurality of different medical diagnosis tests. The control circuitry 124 (or control circuitry 224) may be further configured to determine the coherent health state of the first user 130A. At 416, a plurality of dataset related to the first user 130A may be extracted from the user activities database system 122. The control circuitry 124 (or control circuitry 224) may be further configured to extract the plurality of dataset related to the first user 130A from the user activities database system 122. The plurality of dataset may include tracked daily activities for a plurality of specific timelines that precedes a date and a timepoint on which each medical diagnosis test of the plurality of different medical diagnosis text is conducted.

At 418, a plurality of candidate cause-result pairs may be determined for the determined coherent health state of the first user 130A based on an association of a set of user activities in the extracted plurality of dataset with the cross-correlation of the plurality of results of the plurality of different medical diagnosis tests for the first user 130A. The control circuitry 124 (or control circuitry 224 in the offline mode) may be further configured to determine the plurality of candidate cause-result pairs. At 420, the cross-correlation of the plurality of results of the plurality of different medical diagnosis tests may be calibrated for the first user 130A, based on the determined plurality of candidate cause-result pairs for the determined coherent health state of the first user 130A. The control circuitry 124 (or control circuitry 224 in the offline mode) may be further configured to calibrate the cross-correlation of the plurality of results of the plurality of different medical diagnosis tests.

At 422, a plurality of digital therapeutic environments may be predicted based on the determined coherent health state of the first user 130A and the determined plurality of candidate cause-result pairs. The digital therapeutic environment predictor 206 under the control of the control circuitry 124 (or the control circuitry 224 in offline mode) may be configured to predict the plurality of digital therapeutic environments. At 424, a plurality of impact scores may be determined for a plurality of predicted digital therapeutic environments based on the determined coherent health state of the first user 130A and the determined plurality of candidate cause-result pairs. The impact score generator 208 under the control of the control circuitry 124 (or the control circuitry 224 in offline mode) may be configured to determine the plurality of impact scores.

At 426, a first digital therapeutic environment (e.g. the digital therapeutic environment 116 or 304) may be outputted around the first user 130A based on the predicted digital therapeutic environment associated with a highest impact score from the plurality of impact scores. The digital therapeutic environment generator 214 under the control of the second AI-based system 126 and/or the first AI-based system 120, may be configured to output the first digital therapeutic environment. The first digital therapeutic environment may be a human-sense stimulating mixed reality environment that induces a specific stimulus to the first user 130A for remediation of at least one condition of the determined coherent health state of the first user 130A. At 428, a response to the specific stimulus provided by the output of the first digital therapeutic environment around the first user 130A may be determined. The control circuitry 124 (or control circuitry 224 in the offline mode) may be further configured to determine the response to the specific stimulus provided by the output of the first digital therapeutic environment.

At 430, the plurality of predicted digital therapeutic environments may be updated based on the determined response to the specific stimulus provided by the output of the first digital therapeutic environment around the first user 130A. The control circuitry 124 (or control circuitry 224 in the offline mode) may be further configured to update the plurality of predicted digital therapeutic environments. At 432, a plurality of parameters in the neural network schema 212 of the first AI-based system 120 may be calibrated based on at least the determined response to the specific stimulus provided by the output of the first digital therapeutic environment around the first user 130A. The control circuitry 124 may be further configured to calibrate the plurality of parameters (e.g. weights and features) in the neural network schema 212 of the first AI-based system 120.

At 434, it may be determined whether an alteration is required in a first set of dosages of a first set of medicines prescribed for the at least one condition of the determined coherent health state of the first user 130A, based on the determined response to the specific stimulus provided by the output of the first digital therapeutic environment around the first user 130A. The control circuitry 124 (or control circuitry 224 in the offline mode) may be further configured to determine whether such alteration is required in the first set of dosages of the first set of medicines. At 436, a second set of dosages may be determined for the first set of medicines that may be different from the first set of dosages based on the determined response to the specific stimulus. The control circuitry 124 (or control circuitry 224 in the offline mode) may be further configured to determine the second set of dosages.

At 438, a medicine dosage change recommendation report for the first user may be communicated to a prespecified user device of a health care provider. The medicine dosage change recommendation report may include the second set of dosages for the first set of medicines and a plurality of health indicators related to the determined response to the specific stimulus provided by the output of the first digital therapeutic environment. The control circuitry 124 (or control circuitry 224 in the offline mode) may be further configured to execute such communication. At 440, a sequence of digital therapeutic environments and a time schedule may be predicted in accordance to which each digital therapeutic environment of the sequence of digital therapeutic environments is to be applied on the first user 130A, based on the determined coherent health state of the first user 130A and the determined plurality of candidate cause-result pairs. In some embodiment, instead of one digital therapeutic environment, a sequence of digital therapeutic environments may be predicted and outputted. The robotic system 104 (i.e. the control circuitry 224) may be configured to predict the sequence of digital therapeutic environments and the time schedule.

At 442, the predicted sequence of digital therapeutic environments may be outputted in accordance to the time schedule and a current health state specific to the first user 130A. The outputted sequence of digital therapeutic environments may induce a series of different stimuli specific to the first user 130A for remediation of at least one condition of the determined coherent health state of the first user 130A. The digital therapeutic environment generator 214 may be configured to output the predicted sequence of digital therapeutic environments. At 444, a single sense stimulating output or a multi-sense stimulating output may be generated by the human senses stimulator device 106 to stimulate a specific sense of a plurality of human sense or to concurrently stimulate at least two senses of the plurality of human senses based on a type of control signal received from the robotic system 104. The single sense stimulating output or the multi-sense stimulating output may be generated under the control of the second AI-based system 126 and/or the first AI-based system 120.

At 446, a stimulation request pack may be communicated to the human senses stimulator device 106 to control the human senses stimulator device 106 to contribute at the output of the first digital therapeutic environment. The control circuitry 124 (or control circuitry 224 in the offline mode) may be further configured to execute such communication of the stimulation request pack. The stimulation request pack may include the type of control signal for the single sense stimulating output or the multi-sense stimulating output, a time schedule that defines a specific activation time and a specific duration to generate output, an intensity of output, and a set of sense identifier. Each sense identifier of the set of sense identifiers may indicate a unique specific sense stimulating item to be selected for output in accordance with the time schedule.

While various embodiments described in the present disclosure have been described above, it should be understood that they have been presented by way of example, and not limitation. It is to be understood that various changes in form and detail can be made therein without departing from the scope of the present disclosure. In addition to using hardware (e.g., within or coupled to a central processing unit ("CPU"), microprocessor, micro controller, digital signal processor, processor core, system on chip ("SOC") or any other device), implementations may also be embodied in software (e.g. computer readable code, program code, and/or instructions disposed in any form, such as source, object or machine language) disposed for example in a non-transitory computer-readable medium configured to store the software. Such software can enable, for example, the function, fabrication, modeling, simulation, description and/or testing of the apparatus and methods describe herein. For example, this can be accomplished through the use of general program languages (e.g., C, C++), hardware description languages (HDL) including Verilog HDL, VHDL, and so on, or other available programs. Such software can be disposed in any known non-transitory computer-readable medium, such as semiconductor, magnetic disc, or optical disc (e.g., CD-ROM, DVD-ROM, etc.). The software can also be disposed as computer data embodied in a non-transitory computer-readable transmission medium (e.g., solid state memory any other non-transitory medium including digital, optical, analogue-based medium, such as removable storage media). Embodiments of the present disclosure may include methods of providing the apparatus described herein by providing software describing the apparatus and subsequently transmitting the software as a computer data signal over a communication network including the internet and intranets.

It is to be further understood that the system described herein may be included in a semiconductor intellectual property core, such as a microprocessor core (e.g., embodied in HDL) and transformed to hardware in the production of integrated circuits. Additionally, the system described herein may be embodied as a combination of hardware and software. Thus, the present disclosure should not be limited by any of the above-described exemplary embodiments but should be defined only in accordance with the following claims and their equivalents.

What is claimed is:

1. A personalized health maintenance system, comprising:
    a user activities database system configured to store one or more daily activities of a plurality of users;
    a first artificial intelligence (AI)-based system that comprises one or more processors,
        wherein the first AI-based system is trained based on learning information,
        wherein the learning information is obtained based on at least a response to one or more specific stimulus provided to a digital therapeutic environment by each selected user of a first set of users, and
        wherein the one or more processors are configured to:
            read an input-output data pair of each medical diagnosis test of a plurality of different medical diagnosis tests conducted for a first user;
            convert a format of the input-output data pair of the plurality of different medical diagnosis tests into a format which is readable by the one or more processors;
            determine a coherent health state of the first user based on a correlation of the plurality of different medical diagnosis tests associated with the first user;
            extract a plurality of datasets related to the first user from the user activities database system,
                wherein the plurality of datasets comprises tracked daily activities for a plurality of specific timelines that precedes a date and a timepoint on which each medical diagnosis test of the plurality of different medical diagnosis tests is conducted;
            predict, using a learning technique, a plurality of digital therapeutic environments based on the coherent health data and an association of a set of user activities in the plurality of datasets with a correlation of a plurality of results of the plurality of different medical diagnosis tests; and
    a robotic system that comprises:
        a plurality of movable arms,
            wherein a first movable arm is equipped with a device to generate a magnetic field at varying frequencies, and
            wherein a second movable arm is equipped with a human senses stimulator device;
        a plurality of sensors,
            wherein at least a group of sensors from the plurality of sensors are attached to a body of the first user; and
        a second AI-based system that is communicatively coupled to the first AI-based system,
            wherein the robotic system is configured to:
                output using the human senses stimulator device of the second movable arm, under control of the second AI-based system and the first AI-based system, a first digital therapeutic environment around the first user based on the plurality of digital therapeutic environments that is associated with a highest impact score,
                wherein the first digital therapeutic environment is a human-sense stimulating mixed reality environment that induces a specific stimulus to the first user for remediation of at least one condition of the determined coherent health state of the first user,
                wherein the human-sense stimulating mixed reality environment is a combination of a virtual reality environment and tangible elements that provide a stimulus to a human body or a portion of the human body, and
                wherein the second AI-based system and the first AI-based system are updated based on at least an output provided by one or more of the plurality of sensors to the first digital therapeutic environment output by the human senses stimulator device.

2. The personalized health maintenance system according to claim 1, wherein the plurality of different medical diagnosis tests are conducted from a plurality of different medical equipment that output test results in different data formats, and
    wherein the plurality of different medical diagnosis tests comprises a genetic test, a psychological test, a laboratory based medical diagnosis test, and a non-laboratory based medical diagnosis test.

3. The personalized health maintenance system according to claim 1, wherein the robotic system further comprises an imaging device configured to obtain one or more images of the first user which corresponds to information indicative of facial expressions and gestures of the first user.

4. The personalized health maintenance system according to claim 1,
    wherein the human senses stimulator device is further configured to provide a tangible stimulus,
    wherein the tangible stimulus comprises heat, smell, pressure, cold, sound, and a digital visualization, and wherein the tangible stimulus acts on one or more senses of a plurality of human senses as a part of the digital therapeutic environment.

5. The personalized health maintenance system according to claim 1, wherein the robotic system is further configured to determine a response to the specific stimulus provided by the output of the first digital therapeutic environment around the first user using the plurality of sensors.

6. The personalized health maintenance system according to claim 5, wherein the one or more processors are further configured to update the first AI-based system and the plurality of digital therapeutic environments based on the determined response to the specific stimulus provided by the output of the first digital therapeutic environment around the first user.

7. The personalized health maintenance system according to claim 1, wherein the robotic system is further configured to output, under control of the second AI-based system and the first AI-based system, a sequence of digital therapeutic environments predicted in accordance to a time schedule and a current health state specific to the first user,
wherein the outputted sequence of digital therapeutic environments induces a series of different stimuli specific to the first user for the remediation of at least one condition of the determined coherent health state of the first user.

8. The personalized health maintenance system according to claim 5, wherein the one or more processors are further configured to calibrate a plurality of parameters in a neural network schema of the first AI-based system that is associated with the learning information, based on at least the determined response to the specific stimulus provided by the output of the first digital therapeutic environment around the first user.

9. The personalized health maintenance system according to claim 1, wherein the human senses stimulator device is configured to generate a single sense stimulating output to stimulate a specific sense of a plurality of human senses or a multi-sense stimulating output to concurrently stimulate at least two senses of the plurality of human senses based on a type of control signal received from the robotic system.

10. The personalized health maintenance system according to claim 9, wherein the robotic system is further configured to communicate a stimulation request pack to the human senses stimulator device to control the human senses stimulator device to contribute at the output of the first digital therapeutic environment,
wherein the stimulation request pack comprises the type of the control signal for the single sense stimulating output or the multi-sense stimulating output, a time schedule that defines a specific activation time and a specific duration to generate an output, an intensity of the output, and a set of sense identifiers,
wherein each sense identifier of the set of sense identifiers indicates a unique specific sense stimulating item to be selected for output based on the time schedule.

11. A personalized health maintenance method, comprising:
in a personalized health maintenance system that includes a first artificial intelligence (AI)-based system and a robotic system,
wherein the first AI-based system is trained based on learning information,
wherein the learning information is obtained based on at least a response to one or more specific stimulus provided to a digital therapeutic environment by each selected user of a first set of users,
wherein the first AI-based system comprises one or more processors, and
wherein the method further comprises:
reading, by the one or more processors, an input-output data pair of each medical diagnosis test of a plurality of different medical diagnosis tests conducted for a first user;
converting, by the one or more processors, a format of the input-output data pair the plurality of different medical diagnosis tests into a format which is readable by the one or more processors;
determining, by the one or more processors, a coherent health state of the first user;
based on a correlation of the plurality of different medical diagnosis tests associated with the first user;
extracting, by the one or more processors, a plurality of datasets related to the first user from a user activities database system,
wherein the plurality of datasets comprises tracked daily activities for a plurality of specific timelines that precedes a date and a timepoint on which each medical diagnosis test of the plurality of different medical diagnosis tests is conducted;
predicting, by the one or more processors and using a learning technique, a plurality of digital therapeutic environments based on the coherent health data and an association of a set of user activities in the plurality of datasets with a correlation of a plurality of results of the plurality of different medical diagnosis tests; and
wherein the robotic system comprises:
a plurality of movable arms,
wherein a first movable arm is equipped with a device to generate a magnetic field at varying frequencies, and
wherein a second movable arm is equipped with a human senses stimulator device;
a plurality of sensors,
wherein at least a group of sensors from the plurality of sensors are attached to a body of the first user; and
a second AI-based system that is communicatively coupled to the first AI-based system,
wherein the personalized health maintenance method further comprises:
outputting, by the one or more processors and using the human senses stimulator device of the robotic system and under control of at least the first AI-based system and the second AI-based system, a first digital therapeutic environment around the first user based on the plurality of digital therapeutic environments having a highest impact score,
wherein the first digital therapeutic environment is a human-sense stimulating mixed reality environment configured to induce a specific stimulus to the first user for remediation of at least one condition of the determined coherent health state of the first user,
wherein the human-sense stimulating mixed reality environment is a combination of a virtual reality environment and tangible elements that provide a stimulus to a human body or a portion of the human body, and
wherein the second AI-based system and the first AI-based system are updated based on at least an output provided by one or more of the plurality of sensors to the first digital therapeutic environment output by the human senses stimulator device.

12. The personalized health maintenance method according to claim 11, wherein the method further comprises determining, by the robotic system, a response to the specific stimulus provided by the output of the first digital therapeutic environment around the first user using the plurality of sensors.

13. The personalized health maintenance method according to claim 12, wherein the method further comprises updating the first AI-based system and the plurality of digital therapeutic environments based on the determined response to the specific stimulus provided by the output of the first digital therapeutic environment around the first user.

14. The personalized health maintenance method according to claim 12, wherein the method further comprises calibrating, by the one or more processors, a plurality of parameters in a neural network schema of the first AI-based system that is associated with the learning information, based on at least the determined response to the specific stimulus provided by the output of the first digital therapeutic environment around the first user.

* * * * *